United States Patent [19]

Hashizume et al.

[11] Patent Number: 4,772,748

[45] Date of Patent: Sep. 20, 1988

[54] PROCESS FOR PRODUCING HIGHLY PURE TEREPHTHALIC ACID

[75] Inventors: Hiroshi Hashizume, Kurashiki; Yoshiaki Izumisawa, Kitakyushu, both of Japan

[73] Assignee: Mitsubishi Chemical Industries Limited, Tokyo, Japan

[21] Appl. No.: 845,497

[22] Filed: Mar. 31, 1986

Related U.S. Application Data

[63] Continuation of Ser. No. 556,325, Nov. 30, 1983, abandoned.

[30] Foreign Application Priority Data

Dec. 10, 1982 [JP] Japan ................................. 57-216395

[51] Int. Cl.$^4$ .......................................... C07C 51/265
[52] U.S. Cl. .................................................. 562/413
[58] Field of Search ................ 562/413, 416, 485, 487

[56] References Cited

U.S. PATENT DOCUMENTS 4,286,101  8/1981  Hashizume et al. ................. 562/487

FOREIGN PATENT DOCUMENTS 0018647   1/1982  Japan .................................. 562/413
0035544   2/1982  Japan .................................. 562/416
57-188543 11/1982  Japan .
0200328  12/1982  Japan .................................. 562/413

Primary Examiner—Michael L. Shippen
Attorney, Agent, or Firm—Oblon, Fisher, Spivak, McClelland & Maier

[57] ABSTRACT

Disclosed herein is a process for producing highly pure terephthalic acid which forms polyesters of a particularly favorable color tone, the process comprising the steps of oxidizing p-xylene, thereby obtaining a mixture containing terephthalic acid, subsequently further oxidizing the thus obtained mixture at not higher temperature than that of the first oxidation step, still further oxidizing the reaction mixture of the second oxidation step at a higher temperature than that of the first oxidation step and treating the reaction mixture obtained by the third step of oxidation by bringing thereof into contact with molecular oxygen.

14 Claims, 1 Drawing Sheet

PROCESS FOR PRODUCING HIGHLY PURE TEREPHTHALIC ACID

This application is a continuation of application Ser. No. 556,325, filed Nov. 30, 1983, now abandoned.

BACKGROUND OF THE INVENTION

1. Field of the Invention

The present invention relates to a process for producing highly pure terephthalic acid, and more in detail, the present invention relates to a process for producing highly pure terephthalic acid which can be directly reacted with a glycol component to produce polyesters.

2. Description of the Prior Art

Terephthalic acid is useful as a starting material for producing polyesters, and is ordinarily produced by the so-called SD process wherein p-xylene is brought into reaction with molecular oxygen in the presence of a catalyst containing heavy metal(s) and bromine. However, since 1,000 to 3,000 ppm of 4-carboxybenzaldehyde (hereinafter referred to as 4CBA) is contained as an impurity in the terephthalic acid produced by SD process, it cannot be used as a staring material for producing polyesters used for preparing filaments, films and the like, as it is.

Accordingly, a method has hitherto been adopted, wherein crude terephthalic acid is brought into reaction with methanol to form dimethyl terephthalate, and after purifying thereof, the terephthalate is brought into reaction with a glycol component, or crude terephthalic acid is dissolved in an aqueous solvent at a high temperature and under a high pressure and then the solution is brought into contact with a noble metal catalyst for purification, thereby obtaining the purified terephthalic acid as the starting material for producing polyesters.

Namely, there has been a problem in the above-mentioned processes that in addition to the plant for producing crude terephthalic acid by SD process, it is necessary to provide another plant for purifying the crude terephthalic acid separately.

Accordingly, in recent years, it has become possible to directly produce highly pure terephthalic acid in a single plant by carrying out the oxidation of p-xylene in the presence of a specified catalyst under specified conditions of oxidation, or in a specified oxidation process.

Formerly, the present applicant has proposed an advantageous process for directly producing highly pure terephthalic acid with a content of 4CBA of not more than 500 ppm in a single plant, wherein a reaction mixture which has been obtained by oxidizing p-xylene and contains terephthalic acid is further oxidized subsequently at a temperature lower than that of the first oxidation step and the thus obtained reaction product is further oxidized at a temperature higher than 235° C. (refer to U.S. Pat. No. 4,286,101). The process disclosed in U.S. Pat. No. 4,286,101 is industrially advantageous because of the preparation of highly pure terephthalic acid in a single plant and of the reduced loss of acetic acid as a solvent during the production of terephthalic acid.

Although terephthalic acid obtained by the above-mentioned process is satisfactorily usable as a commercial starting material for producing polyesters for use in preparing, for instance, fibers, films and the like because of its low content of 4CBA and its high transmissivity, as a result of the present inventors' studies for processes of obtaining terephthalic acid of a higher quality, they have found that terephthalic acid obtained from a specified treatment of the reaction mixture obtained by the third step of oxidation forms the polyesters particularly excellent in its colour tone in spite of the fact that the content of 4CBA and transmissivity are nearly the same with the above-mentioned process, and have been attained to the present invention.

Namely, the object of the present invention is to provide a process for continuously producing highly pure terephthalic acid which gives polyesters excellent in its colour tone.

SUMMARY OF THE INVENTION

In an aspect of the present invention, there is provided a process for continuously producing highly pure terephthalic acid, comprising the step of (1) oxidizing more than 95% by weight of the supplied amount of p-xylene in acetic acid solvent by molecular oxygen at a temperature of 180° to 230° C. in the presence of a catalyst composed of heavy metals and bromine thereby obtaining reaction mixture containing terephthalic acid, (2) subsequently further oxidizing the thus obtained reaction mixture by molecular oxygen at not higher temperature than that of the first oxidation step, (3) still further oxidizing the reaction mixture obtained in the second oxidation step by molecular oxygen at a higher temperature than that of the first oxidation step, (4) contacting the reaction mixture obtained in the third oxidation step with molecular oxygen at a temperature of 160° to 230° C., and (5) collecting the thus formed terephthalic acid from the thus treated reaction mixture.

BRIEF EXPLANATION OF THE DRAWING

Of the attached drawing.

DETAILED DESCRIPTION OF THE PREFERRED EMBODIMENTS

Figure 1:
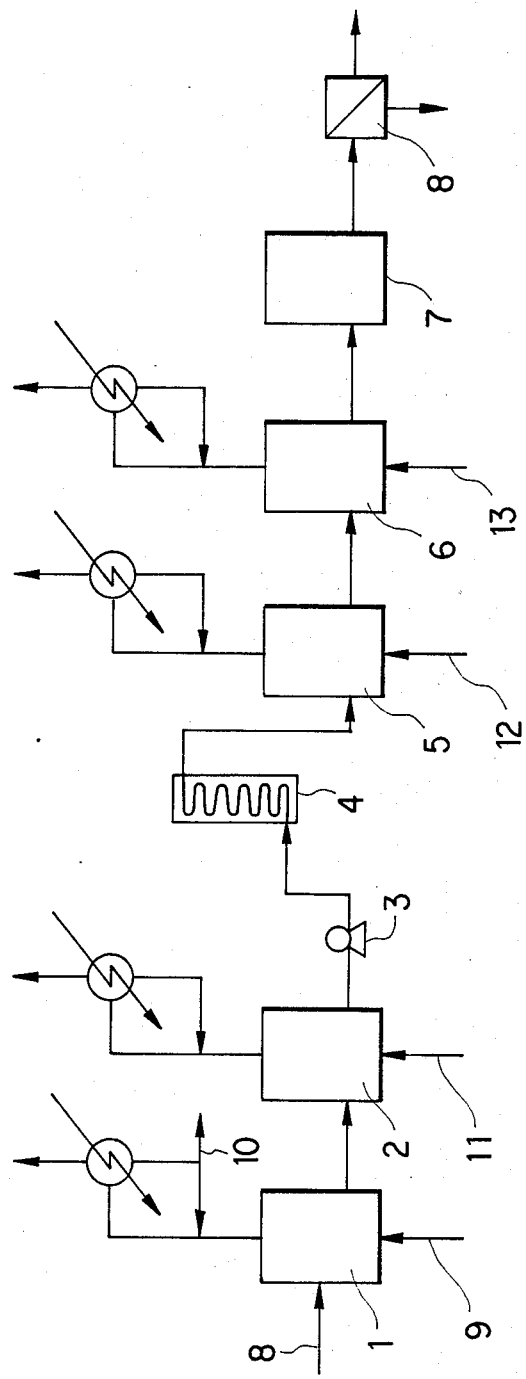
FIG. 1 shows a flow chart of a series of reaction apparatus used in Examples and Comparative Examples.

The present invention relates to a process for producing highly pure terephthalic acid which can be directly reacted with a glycol component to produce polyesters.

The process for producing highly pure terephthalic acid according to the present invention comprises reacting p-xylene with molecular oxygen in acetic acid solvent in the presence of a catalyst containing heavy metals and bromine.

The process according to the present invention is precisely explained as follows.

In the first step, in the first reaction vessel provided with a stirrer, ordinarily not less than 95% by weight, preferably not less than 98% by weight of the supplied amount of p-xylene is oxidized into terephthalic acid in acetic acid solvent in the presence of a catalyst containing heavy metals and bromine ordinarily at a reaction temperature of 180° to 230° C., preferably 190° to 210° C. under a pressure of a few kilograms/cm$^2$G to 100 kg/cm$^2$G, preferably 10 to 30 kg/cm$^2$G. At a lower temperature, it is impossible to sufficiently oxidize p-xylene, and on the other hand, at a higher temperature, not only is it impossible to obtain highly pure terephthalic acid but also the combustion loss of the solvent, acetic acid, increases, thus leading to undesirable results. It is necessary to carry out the reaction in the first reaction vessel for a time period during which not less than 95% by weight of the supplied amount of p-xylene is oxidized into terephthalic acid, and ordinarily, the reaction is carried out for 30 to 200 min, preferably 40 to 150 min. In the present oxidation, almost all the thus formed terephthalic acid separates as crystals out of the solvent.

The catalyst system used according to the present invention ordinarily includes the following three elements, cobalt, manganese and bromine. For instance, a cobalt compound at a concentration of 120 to 600 ppm, preferably 150 to 400 ppm calculated as metallic cobalt in the above-mentioned solvent, a manganese compound in an amount of 0.5 to 1.5 times of that of metallic cobalt calculated as metallic manganese and a bromine compound at a concentration of 500 to 2,000 ppm, preferably 600 to 1,500 ppm calculated as bromine in the solvent are used in the reaction. As the concrete examples of these compounds, cobalt compounds such as cobalt acetate, cobalt naphthenate and the like, manganese compounds such as manganese acetate, manganese naphthenate and the like, and bromine compounds such as hydrogen bromide, sodium bromide, cobalt bromide, manganese bromide and the like may be mentioned. In addition, in the case of using manganese bromide or cobalt bromide, one compound can serve the role of two components of the catalyst.

The weight ratio of the solvent to p-xylene in the mixture supplied to the first reaction vessel is ordinarily 2 to 6:1, and the use of the solvent in an amount corresponding to that of below the above-mentioned ratio is not desirable, because a favorable stirring of the reaction mixture cannot be favorably effected and the favorable oxidation in the second step of oxidation at a higher reaction temperature cannot be desirably carried out.

In addition, the solvent may contain an amount of water, for instance, of not more than 20% by weight of the solvent.

As molecular oxygen supplied into the liquid phase in the first reaction vessel, air may be ordinarily used at a molar ratio of molecular oxygen to p-xylene of 3 to 100:1, and the air is supplied ordinarily so that the concentration of oxygen in the exhaust gas from the first reaction vessel is 1.5 to 8% by volume.

In the first oxidation step, the concentration of water within the reaction vessel may be controlled to a low level, for instance, 5 to 15% by weight by drawing a part of the condensate obtained by cooling the condensable gas evaporated from the liquid phase in the reaction vessel, out from the system without returning to the reaction vessel.

In addition, according to the present invention, it is preferable to maintain the concentration of 4CBA in the reaction mother liquor at 1,000 to 3,000 ppm by controlling the temperature, the pressure, the retention time of the reactants and the composition of the catalyst in the first reaction vessel. The lower the concentration of 4CBA in the reaction mother liquor, the better chance the higher purity of terephthalic acid are obtained. However, on the other hand, in the case where the reaction is carried out under the conditions for reducing the concentration of 4CBA, the amount of combustion of acetic acid solvent tends to increase.

According to the present invention, however, since highly pure terephthalic acid can be obtained ultimately by the second oxidation step and third oxidation step which will be described later even in the case where the concentration of 4CBA in the first reaction mother liquor is kept at a value as high as a certain extent, it is possible to remarkably suppress the combustion of acetic acid solvent, in the first reaction vessel.

In the next step, the slurry-like reaction mixture obtained in the first reaction vessel is supplied to the second reaction vessel, for instance, a vessel provided with a stirrer, and subjected to the second oxidation step by molecular oxygen at a temperature lower than that of the reaction temperature in the first reaction vessel by 0° to 50° C., preferably 2° to 30° C. ordinarily without further supplying p-xylene, however, a small amount of p-xylene may be additionally supplied within such range as not to interfere with the reaction of the second oxidation step.

By such a treatment in the second reaction vessel, mainly the intermediates of oxidation contained in the reaction mother liquor is oxidized, however, at a lower temperature than that mentioned above, it is impossible to oxidize the intermediates satisfactorily. On the other hand, at a higher temperature than the reaction temperature in the first reaction vessel, it is also undesirable because of the formation of impurities which become colouring components of the product, terephthalic acid. In addition, the reaction time of the second oxidation step is ordinarily 5 to 90 min, preferably 15 to 60 min.

Since the amount of substances to be oxidized in the second oxidation step is small, the amount of molecular oxygen supplied to the second reaction vessel is one tenth to one thousandth of that supplied to the first reaction vessel, and is preferably the amount so that the content of oxygen in the exhaust gas from the second reaction vessel is ordinarily 1 to 8% by volume, preferably 2 to 6% by volume. As molecular oxygen, atmospheric air is used with or without diluting by an inert gas.

The reaction mixture thus treated in the second reaction vessel is subsequently supplied to the third reaction vessel provided with a stirrer, and subjected to the third oxidation step at a temperature higher than the reaction temperature in the first reaction vessel by molecular oxygen ordinarily without additionally supplying p-xylene.

In the third oxidation step, intermediates of oxidation which have been included within the particles mainly composed of terephthalic acid are extracted into the reaction mother liquor and subjected to oxidation. In the case where the temperature in the third reaction vessel is too low, the extraction of the intermediates of oxidation from the particles mainly composed of terephthalic acid is not carried out favorably. On the other hand, in the case where the temperature is too high, not only it is uneconomical from the view point of energy but also there is a fear of forming coloured impurities. Accordingly, the third oxidation step is carried out ordinarily at a temperature of 235° to 290° C., preferably 240° to 280° C.

Concerning the reaction pressure, since it is necessary to keep the reaction mixture in a state of liquid phase, the third oxidation step is carried out industrially under a pressure of 30 to 100 kg/cm$^2$G. In addition, the retention time in the third oxidation step is 5 to 120 min, preferably 10 to 60 min.

Since in the third oxidation step, the content of the substance to be oxidized remaining in the reaction mixture is very small, and the reaction temperature is relatively high, too large amount of supplied molecular oxygen tends to raise the amount of combustion of the acetic acid solvent. Accordingly, molecular oxygen is supplied in an amount of 0.003 to 0.3 mol, preferably 0.01 to 0.1 mol per one mol of terephthalic acid in the reaction mixture supplied to the third reaction vessel, and it is preferable to adjust the reaction conditions so that the concentration of oxygen in the exhaust gas from the third reaction vessel is substantially zero, in other words, not more than 0.5% by volume. As molecular oxygen, ordinarily atmospheric air is used with or without diluting by an inert gas.

In the present invention, a contact treatment of the reaction mixture obtained in the third oxidation step, by bringing thereof into contact with molecular oxygen is carried out at a temperature of 160° to 230° C., preferably 180° to 220° C. This temperature is ordinarily preferable to be lower than the temperature of the third oxidation step by 10° C. or more.

According to the present invention, by the contact treatment, it is possible to obtain terephthalic acid which gives polyesters excellent in the colour tone, although the content of 4CBA and the transmissivity of the thus obtained terephthalic acid are not so much different from those of the product obtained in the third oxidation step, omitting the contact treatment. At a lower temperature in the contact treatment, the expected effect in the present invention cannot be satisfactorily obtained. On the other hand, at a higher temperature, it is undesirable because of the increased amount of combustion of acetic acid solvent. As molecular oxygen used in the contact treatment, ordinarily atmospheric air is used with or without diluting by an inert gas, and the amount of molecular oxygen used in the contact treatment is 0.001 to 0.1 mol per one mol of terephthalic acid contained in the reaction mixture supplied from the third oxidation step, and the amount is controlled so that the concentration of oxygen in the exhaust gas from the vessel in which the contact treatment is carried out is, for instance, 1 to 8% by volume, preferably 2 to 6% by volume.

The vessel for use in the contact treatment is ordinarily a similar type to the reaction vessel used for oxidation and provided with a stirrer.

Since in the contact treatment, substantial oxidation of the intermediates of oxidation, contained in the reaction mixture supplied to the vessel for the contact treatment, does not occur, it is preferable not to add any amount of p-xylene and the catalyst in the reaction mixture from the third oxidation step.

The time of contact in the contact treatment is ordinarily 5 to 120 min, preferably 5 to 60 min.

In addition, in the reaction mixture obtained after the completion of the third oxidation step, 50 to 99% by weight of the total amount of telephthalic acid formed in the oxidation steps is present as crystals and the remainder has been dissolved. Accordingly, after cooling the reaction mixture and making the dissolved terephthalic acid crystalize out from the reaction mixture, the thus treated reaction mixture is subjected to the step of separation of terephthalic acid.

In the case where the contact treatment according to the present invention is carried out in the apparatus for crystallization which is ordinarily provided before the apparatus for separation of terephthalic acid, it is desirable because it is not necessary to provide a new apparatus. In other words, by blowing the necessary amount of molecular oxygen into the already provided apparatus for crystallization, the effect of the present invention is sufficiently attained.

As has been described above, in the process according to the present invention, the reaction mixture obtained by oxidizing not less than 95% by weight of p-xylene in the first oxidation step is subjected further to oxidation in the second oxidation step at not higher temperature than that in the first oxidation step, and after subjecting the thus obtained reaction mixture in the second oxidation step still further to oxidation in the third oxidation step at a temperature higher than that in the first oxidation step, the reaction mixture thus obtained in the third oxidation step is treated by bringing thereof into contact with molecular oxygen at a temperature of 160° to 230° C. As the apparatus for use in the respective oxidation steps and in the contact treatment, a reaction vessel provided with a reflux condenser in the upper part thereof and provided with a stirrer may be mentioned in ordinary case. The number of stages of treatment in each oxidation step or the treatment may be one, however, according to necessity, the second oxidation step, the third oxidation step and the contact treatment step according to the present invention may have a plurality of stages, respectively. In addition, the reaction mixture obtained in the second oxidation step is ordinarily introduced into the high pressure part of the reaction system under a pressure via a pump and heated therein for subjecting to the subsequent third oxidation step. In this case, the heating can be carried out by a heat-exchanger of monotubular type or multitubular type.

After ending the contact treatment of contacting the reaction mixture obtained in the third oxidation step with molecular oxygen, not less than about 95% by weight of the total amount of terephthalic acid formed in the three oxidation steps crystallizes out from the liquid phase, and ordinarily, the rest portion of terephthalic acid still remaining as a solute in the liquid phase is crystallized out by cooling the reaction mixture, and then the whole materials are supplied to the separation step. However, according to circumstances, after subjecting the reaction mixture of the third oxidation step to the contact treatment of the present invention, the thus treated reaction mixture may be directly supplied to the separation step without being cooled.

The step of crystallization is carried out in a plurality of stages, namely, the temperature and the pressure of the whole system are gradually and slowly reduced. In the next place, the thus treated reaction mixture is subjected to separation of crystals by, for instance, centrifugation for collecting the crystals of terephthalic acid. The thus separately collected crystals of terephthalic acid are, as occasion demands, for instance, washed with water or acetic acid and then dried to be a product. On the other hand, the reaction mother liquor is sent ordinarily to a distilling tower wherein the catalyst, the by-product and water formed in the oxidation are removed from the reaction mixture to recover acetic acid. Since in the process according to the present invention, the amount of the by-products, particularly that of the impurities which disturb oxidation of p-xylene is very small, about 10 to 80% by weight of the reaction mother liquor may be recycled to the first reaction vessel.

In the case of producing highly pure terephthalic acid of a content of 4CBA of not more than 500 ppm in a single plant according to the process of the present invention, it is possible to produce terephthalic acid which gives polyesters of particularly favorable in the colour tone thereof, and accordingly, the process of the present invention is extremely advantageous industrially and economically.

The present invention will be explained more in detail while referring to the following nonlimitative Examples, in addition, "part" in Examples represents "part by weight".

EXAMPLES 1 to 3:

The reactions according to the process of the present invention were carried out while using the apparatus shown in a flow chart of FIG. 1.

Into the first reaction vessel 1 made of pressure-resistant titanium and provided with a reflux condenser, a stirrer, an inlet of the starting materials and the solvent, an inlet of air and an outlet for drawing out the slurry-like reaction mixture, a mixture consisting of one part of p-xylene, 4.5 parts of acetic acid containing 5% by weight of water, 0.0032 part of cobalt acetate tetrahydrate, 0.0034 part of manganese acetate tetrahydrate and 0.0049 part of 47% by weight of hydrobromic acid was supplied per an hour from the inlet of the starting materials and the solvent through a pipe 8, and by supplying air as an oxidizing gas from the inlet of air through a pipe 9, liquid phase oxidation of p-xylene was carried out at a temperature of 200° C. and under a pressure of 18 kg/cm$^2$G at a retention time of 90 min while adjusting the concentration of oxygen in the exhaust gas from the reaction vessel to 4% by volume and drawing 1.5 part of the refluxed liquid out from the system through the pipe 10 so that the content of water in the reaction vessel 1 is controlled to about 10% by weight.

The reaction mixture from the first reaction vessel 1 was continuously supplied to the second reaction vessel 2 which was provided with the same attachments as in the first reaction vessel 1, and was subjected to the second oxidation step under the conditions of a reaction temperature of 185° C., a pressure of 11 kg/cm$^2$G and a retention time of 30 min by supplying air so that the concentration of oxygen in the exhaust gas from the second reaction vessel is 4% by volume.

The reaction mixture from the second reaction vessel 2 was, after raising the pressure thereof to 55 kg/cm$^2$G by a boosting pump 3, supplied to a monotubular heater 4 to raise the temperature thereof to 260° C. and then further supplied to the third reaction vessel 5 provided with the same attachments as in the first reaction vessel 1. The thus supplied reaction mixture was subjected to the third oxidation step under the conditions of a temperature of 260° C., a pressure of 55 kg/cm$^2$G and a retention time of 30 min while supplying 0.07 part of air per one hour from the air inlet through the pipe 12.

The reaction mixture from the third reaction vessel 5 was supplied to the vessel 6 provided with the same attachments as in the first reaction vessel 1 and 0.009 part of air was supplied per one hour from the air linlet through the pipe 13 under the conditions shown in Table 1 so that the concentration of oxygen in the exhaust gas from the vessel 6 was 4% by volume.

The reaction mixture obtained by the consecutive treatments of oxidation and the contact treatment with molecular oxygen-contact was cooled in the crystallization vessel 7 to crystallize terephthalic acid, and then subjected to centrifugal separation in the centrifugal machine 8 for collecting the crystals of terephthalic acid.

The thus obtained terephthalic acid was analyzed on the content of 4CBA thereof and the transmissivity at 340 nm thereof, and polyethylene terephthalate was prepared therefrom to determine the colour tone of the thus obtained polymer (expressed by b-value). The results of the analyses are shown also in Table 1.

COMPARATIVE EXAMPLE 1

The same procedures as in Example 1 were carried out except for omitting the contact treatment in the vessel 6 of contacting the reaction mixture obtained in the third oxidation step with molecular oxygen in the vessel 6. The results are also shown in Table 1.

COMPARATIVE EXAMPLE 2

The same procedures as in Example 1 were carried out except for the temperature at the contact treatment in the vessel 6 of 150° C. instead of 200° C. in Example 1. The results are also shown in Table 1.

TABLE 1

| Specimen prepared in | Conditions of treatment in the vessel 6 | | | | Quality of terephthalic acid | | Colour tone of polymer b-value[3] |
|---|---|---|---|---|---|---|---|
| | Temperature (°C.) | Pressure (kg/cm$^2$ G) | Retention time (min) | O$_2$ blowing (yes or no) | Content[1] (ppm) | Trans[2] (%) | |
| Example 1 | 200 | 11 | 15 | yes | 280 | 90.0 | 1.8 |
| Example 2 | 200 | 11 | 45 | yes | 280 | 90.0 | 1.7 |
| Example 3 | 180 | 7.5 | 15 | yes | 290 | 88.5 | 2.2 |
| Comparative Example 1 | 200 | 11 | 15 | no | 280 | 89.0 | 3.8 |
| Comparative Example 2 | 150 | 3.5 | 15 | yes | 330 | 81.0 | 6.1 |

Notes:
[1]Content of 4CBA
[2]Transmissivity at 340 nm
[3]Refer to the next page.

Method for measuring the colour tone(b-value) of polymer

A mixture of 30 mols of terephthalic acid and 60 mols of ethylene glycol was subjected to esterification in the presence of 0.003 mol of antimony trioxide, 0.0024 mol of cobalt acetate, 0.0058 mol of triethyl phosphate and 0.015 mol of titanium oxide under the conditions of a temperature of 235° C. and a pressure of 2.5 kg/cm$^2$G for 120 min, and then the reaction mixture was heated to 280° C. for 120 min while reducing the pressure of the reaction system so as to obtain a polymer of the degree of polymerization [η] of 0.69.

After filling a quartz cell with the chips of the thus obtained polymer, the b-value of the polymer was measured by a colour difference meter (made by TOKYO DENSHOKU CO., Ltd., Model: TC-55 D). For reference, b-values with a sign of "+" mean yellow tone, and those with a sign of "−" mean blue tone. The smaller is the b-value of a polymer, the better is the colour tone of the polymer.

What is claimed is:

1. A process for continuously producing highly pure terephthalic acid, comprising the steps of:
   (a) oxidizing, as the first oxidation step, not less than 95% by weight of the supplied amount of p-xylene in acetic acid solvent by molecular oxygen at a temperature of 180° to 230° C. in the presence of a catalyst composed of heavy metals and bromine, thereby obtaining a reaction mixture containing terephthalic acid,
   (b) subsequently further oxidizing, as the second oxidation step, the thus obtained reaction mixture by molecular oxygen at a temperature of not higher than that of said first oxidation step,
   (c) still further oxidizing, as the third oxidation step, the reaction mixture obtained in said second oxidation step by molecular oxygen at a temperature of 235° to 290° C., in which the molar ratio of supplied oxygen for said third oxidation step to terephthalic acid in the reaction mixture obtained in said second oxidation step is 0.003:1 to 0.3:1, so that the concentration of oxygen in the exhaust gas of said third oxidation step is less than 0.5% by volume,
   (d) contacting the reaction mixture obtained in said third oxidation step with molecular oxygen at a temperature of 160° to 230° C. so that the concentration of oxygen in the exhaust gas which exits the step (d) contacting step while contacting said reaction mixture with molecular oxygen is 1 to 8% by volume, and
   (e) collecting the thus formed terephthalic acid from the thus treated reaction mixture.

2. A process according to claim 1, wherein the molar ratio of molecular oxygen supplied for said first oxidation step to p-xylene is 3 to 100:1.

3. A process according to claim 1 or 2, wherein the concentration of oxygen in the exhaust gas of said first oxidation step is 1.5 to 8% by volume.

4. A process according to claim 1, wherein the temperature of said second oxidation step is lower than that of said first oxidation step by 0° to 50° C.

5. A process according to claim 1, wherein the temperature of said second oxidation step is lower than that of said first oxidation step by 2° to 30° C.

6. A process according to claim 1 or 4, wherein the amount of supplied oxygen for said second oxidation step is one tenth to one thousandth of that for said first oxidation step.

7. A process according to claim 1, 4, or 5 wherein the concentration of oxygen in the exhaust gas of said second oxidation step is 1 to 8% by volume.

8. A process according to claim 1, wherein said catalyst for use in the oxidation steps of p-xylene is a catalytic system comprising a cobalt compound in amount of 120 to 600 ppm as metallic cobalt to said solvent, a manganese compound in an amount of 0.5 to 1.5 times as metallic manganese of the amount of said cobalt compound as metallic cobalt and a bromine compound in an amount of 500 to 2,000 ppm as bromine to said solvent.

9. A process according to claim 1, wherein the concentration of 4CBA in the reaction mother liquor during the reaction in said first oxidation step is kept at 1,000 to 3,000 ppm.

10. A process according to claim 1, wherein the reaction mixture obtained in said third oxidation step is contacted with molecular oxygen at a temperature lower than the temperature of said third oxidation step by not less than 10° C.

11. A process according to claim 1, wherein the molar ratio of molecular oxygen to be contacted with the reation mixture obtained in said third oxidation step to terephthalic acid contained in the reaction mixture obtained in said third oxidation step is 0.001 to 0.1:1.

12. A process according to claim 1, 10 or 11, wherein the contacting time of the reaction mixture obtained in said third oxidation step with molecular oxygen is 5 to 120 min.

13. A process according to claim 1, 10 or 11, wherein the reaction mixture obtained in said third oxidation step is contacted with molecular oxygen without newly adding p-xylene and said catalyst.

14. A process according to claim 1, wherein more than 95% by weight of terephthalic acid contained in the reaction mixture after a termination of contacting the reaction mixture obtained in the third oxidation step with molecular oxygen is separated out as crystals from the liquid phase.

* * * * *